US00RE45573E

(19) United States
(12) Reissued Patent
Kakiya et al.

(10) Patent Number: US RE45,573 E
(45) Date of Reissued Patent: Jun. 23, 2015

(54) PROCESS FOR PRODUCING IMIDE COMPOUND

(75) Inventors: Yuzo Kakiya, Ibaraki (JP); Mayumi Oda, Osaka (JP)

(73) Assignee: Sumitomo Dainippon Pharma Co., Ltd., Osaka (JP)

(21) Appl. No.: 14/137,464

(22) Filed: Dec. 20, 2013

Related U.S. Patent Documents

Reissue of:
(64) Patent No.: 7,605,260
Issued: Oct. 20, 2009
Appl. No.: 10/565,105
PCT Filed: Jul. 27, 2004
PCT No.: PCT/JP2004/011035
§ 371 (c)(1),
(2), (4) Date: Jan. 19, 2006
PCT Pub. No.: WO2005/009999
PCT Pub. Date: Feb. 3, 2005

(30) Foreign Application Priority Data

Jul. 29, 2003 (JP) ..... 2003-281860

(51) Int. Cl.
*C07D 401/14* (2006.01)
*C07D 241/04* (2006.01)
*C07D 295/00* (2006.01)

(52) U.S. Cl.
CPC ..... *C07D 401/14* (2013.01); *C07D 295/00* (2013.01)

(58) Field of Classification Search
None
See application file for complete search history.

(56) References Cited

U.S. PATENT DOCUMENTS

| | | | |
|---|---|---|---|
| 4,479,954 | A | 10/1984 | Hirose et al. |
| 4,978,752 | A | 12/1990 | Maeda et al. |
| 5,532,372 | A | 7/1996 | Saji et al. |
| 5,663,381 | A | 9/1997 | Schickaneder et al. |
| 5,780,632 | A | 7/1998 | Saji et al. |
| 6,673,942 | B1 | 1/2004 | Kottenhahn et al. |

FOREIGN PATENT DOCUMENTS

| | | | | |
|---|---|---|---|---|
| CN | 1020611 | C | 5/1993 | |
| JP | 5-17440 | A | 1/1993 | |
| WO | WO-96/33185 | A1 | 10/1996 | |
| WO | WO-01/58835 | A1 | 8/2001 | |
| WO | 02/53140 | * | 7/2002 | ..... A61K 31/00 |

* cited by examiner

*Primary Examiner* — Noble Jarrell
(74) *Attorney, Agent, or Firm* — Finnegan, Henderson, Farabow, Garrett & Dunner, LLP

(57) ABSTRACT

The present invention provides an excellent industrial process for producing an imide compound hydrochloride.
The process for producing an imide compound hydrochloride of the formula (2):

(2)

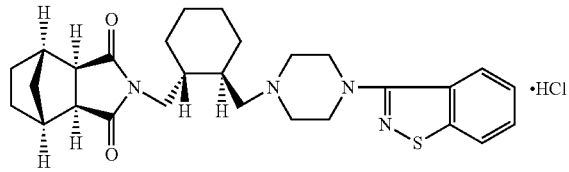

or an enantiomer thereof,
which comprises treating a compound of the formula (1):

(1)

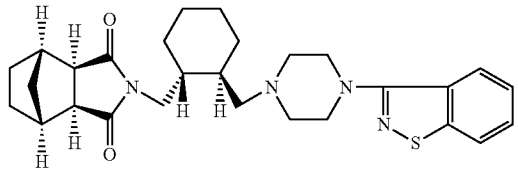

or an enantiomer thereof with an aqueous hydrochloric acid solution in a hydrophilic solvent, followed by crystallizing the resultant.

12 Claims, No Drawings

PROCESS FOR PRODUCING IMIDE COMPOUND

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a reissue application of U.S. Pat. No. 7,605,260, issued on Oct. 20, 2009, from U.S. patent application Ser. No. 10/565,105, which is the National Stage Entry of International Application No. PCT/JP2004/011035, filed Jul. 27, 2004, which claims the benefit of priority of Japan Application No. 2003-281860, filed on Jul. 29, 2003, all of which are incorporated herein by reference in their entirety.*

TECHNICAL FIELD

The present invention relates to a process for producing an imide compound of the formula (2) or an enantiomer thereof, which is useful as a psychotropic substance.

(2)

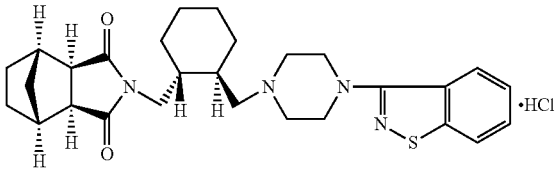

BACKGROUND ART

It has been reported that the imide compound hydrochloride of the above formula (2) can be produced by treating an imide compound in free form of the formula (1):

(1)

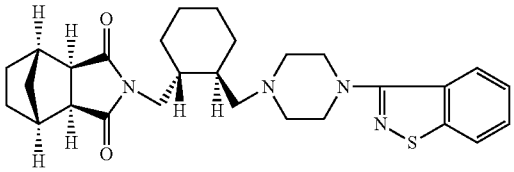

with a hydrogen chloride 2-propanol solution in acetone, and crystallizing the resultant. However, said process is not sufficient enough for an industrial process from the aspect of the availability and the handling of the reagents to be used therein (cf., JP-A-5-17440).

DISCLOSURE OF INVENTION

An object of the present invention is to provide an excellent industrial process for producing the above imide compound hydrochloride.

The present inventors have intensively studied in order to solve the above-mentioned problems, and found that the imide compound hydrochloride of the above formula (2) can be obtained in high quality and high yield under moderate and simple reaction conditions by treating the compound of the above formula (1) with an aqueous hydrochloric acid solution in a hydrophilic solvent, and crystallizing the resultant, and they have accomplished the present invention.

Namely, the present invention relates to the following:

[1] A process for producing an imide compound hydrochloride of the formula (2):

(2)

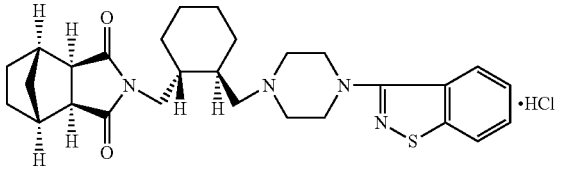

or an enantiomer thereof, which comprises treating a compound of the formula (1):

(1)

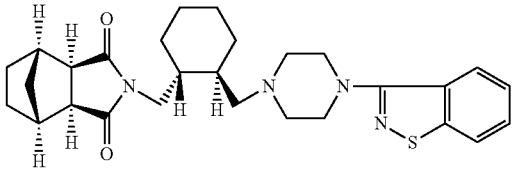

or an enantiomer thereof with an aqueous hydrochloric acid solution in a hydrophilic solvent, and crystallizing the resultant.

[2] The process for producing the imide compound hydrochloride according to the above [1], wherein the hydrophilic solvent is a ketone solvent.

[3] The process for producing the imide compound hydrochloride according to the above [1], wherein the hydrophilic solvent is acetone.

[4] The process for producing the imide compound hydrochloride according to any one of the above [1], [2] and [3], wherein the aqueous hydrochloric acid solution is a 1.8-14.4% aqueous hydrochloric acid solution.

[5] The process for producing the imide compound hydrochloride according to any one of the above [1], [2] and [3], wherein the aqueous hydrochloric acid solution is a 3.0-5.0% aqueous hydrochloric acid solution.

The imide compound hydrochloride of the above formula (2) or an enantiomer thereof (hereinafter, occasionally simply referred to as the imide compound hydrochloride of the formula (2) or the imide compound hydrochloride (2)) can be produced by treating a solution of the compound of the above formula (1) or an enantiomer thereof (hereinafter, occasionally simply referred to as the compound of the formula (1) or the compound (1)) in a hydrophilic solvent with an aqueous hydrochloric acid solution, and crystallizing the resultant. The compound of the formula (1) can be produced according to the method disclosed in JP-A-5-17440.

The hydrophilic solvent includes, for example, ketone solvents, ether solvents, and alcohol solvents, and preferable ones are ketone solvents.

The ketone solvent includes, for example, dialkyl ketones having not more than 6 carbon atoms such as acetone, methyl ethyl ketone, 4-methyl-2-pentanone, etc. Preferable ones are acetone, methyl ethyl ketone, and most preferable one is acetone.

The ether solvent includes, for example, cyclic ethers having not more than 6 carbon atoms such as tetrahydrofuran, dioxane, etc., and acyclic dialkyl ethers having not more than 6 carbon atoms such as dimethyl ether, diethyl ether, etc. Preferable one is tetrahydrofuran.

The alcohol solvent includes, for example, alcohols having not more than 6 carbon atoms such as 2-propanol, ethanol, methanol, ethylene glycol, etc., and preferable one is 2-propanol.

The hydrophilic solvent is usually used in an amount of 3 to 100 times (by weight) of the amount of the compound (1), preferably in an amount of 5 to 30 times (by weight) of the amount of the compound (1), and more preferably in an amount of 7 to 15 times (by weight) of the amount of the compound (1).

The temperature for dissolving the compound (1) in a hydrophilic solvent is usually in the range of 0° C. to a reflux temperature, preferably in the range of 25° C. to a reflux temperature. For the solvents other than ether solvents, the temperature is more preferably in the range of 45° C. to a reflux temperature.

The concentration of hydrogen chloride in the aqueous hydrochloric acid solution is not necessarily specified. For example, an aqueous hydrochloric acid solution in a concentration of 0.3-36% may be exemplified. The concentration of hydrogen chloride in the aqueous hydrochloric acid solution is preferably a 1.8 to 14.4% aqueous hydrochloric acid solution, more preferably about 3.0 to 5.0% aqueous hydrochloric acid solution, from view point of (i) the amount of the hydrophilic solvent contained in the crystals of the imide compound hydrochloride, (ii) the amount of the impurities contained in the crystals of the imide compound hydrochloride, and (iii) the yield (see Table 1).

The equivalents of the hydrochloric acid to be used is usually in the range of 0.9 to 3 equivalents, preferably in the range of 1.0 to 2.0 equivalents, more preferably in the range of 1.0 to 1.3 equivalent, to one equivalent of the compound (1).

The temperature for treating the compound (1) with an aqueous hydrochloric acid solution in a hydrophilic solvent and crystallizing the resultant is not necessarily specified, and these processes may be carried out either under cooling or warming. The reaction temperature is usually in the range of 0° C. to a reflux temperature, preferably in the range of 25° C. to a reflux temperature, and more preferably in the range of 50° C. to a reflux temperature.

The method for mixing a solution of the compound (1) in a hydrophilic solvent and an aqueous hydrochloric acid solution is not necessarily specified. For example, a method of adding an aqueous hydrochloric acid solution into a solution of the compound (1) in a hydrophilic solvent, a method of adding a solution of the compound (1) in a hydrophilic solvent into an aqueous hydrochloric acid solution, a method of simultaneously adding both a solution of the compound (1) in a hydrophilic solvent and an aqueous hydrochloric acid solution into the reactor vessel, a method of adding a mixture of an aqueous hydrochloric acid solution and a hydrophilic solvent into a solution of the compound (1) in a hydrophilic solvent, a method of adding a solution of the compound (1) in a hydrophilic solvent into a mixture of an aqueous hydrochloric acid solution and a hydrophilic solvent, etc. are exemplified.

The time to be needed for mixing a solution of the compound (1) in a hydrophilic solvent and an aqueous hydrochloric acid solution is not necessarily specified. For example, a method of mixing both solutions at once, a method of mixing by adding one of them into the other with spending an extended period of time, are exemplified. A method of mixing by adding one of them into the other with spending an extended period of time is usually employed. In this case, the time to be needed is, for example, in the range of from one minute to 6 hours, preferably in the range of from 3 minutes to 3 hours.

The crystals of the imide compound hydrochloride precipitated by treatment with hydrochloric acid are separated by a conventional method, for example, by filtration, to give the imide compound hydrochloride of the above formula (2). The temperature of the reaction slurry prior to the filtration is not necessarily specified, and the filtration is usually carried out after the reaction slurry is sufficiently crystallized by cooling or warming. The temperature for keeping the reaction slurry is usually in the range of −20° C. to 60° C., preferably in the range of −10° C. to 25° C., more preferably in the range of 0 to 10° C.

The imide compound hydrochloride (2) thus separated may be obtained in the solvent-free form by drying. The drying method is not necessarily specified, for example, drying under reduced pressure, drying under atmospheric pressure, drying with aeration of inert gas such as nitrogen or air flow. The drying temperature is not necessarily specified, and the drying is carried either under cooling or warming, preferably at a temperature of 0 to 50° C.

The imide compound hydrochloride represented by the above formula (2) has been known to be useful as an agent for treatment of schizophrenia, etc. (cf., JP-A-5-17440).

By using an aqueous hydrochloric acid solution, which is easily obtained and excellent in safety and operability, without a necessity to produce from a hydrochloric acid gas and a solvent by mixing them like hydrochloric acid/solvent system, the industrially advantageous production of the imide compound hydrochloride becomes possible.

The present invention is illustrated in more detail by Examples, but the present invention should not be construed to be limited thereto.

EXAMPLE 1

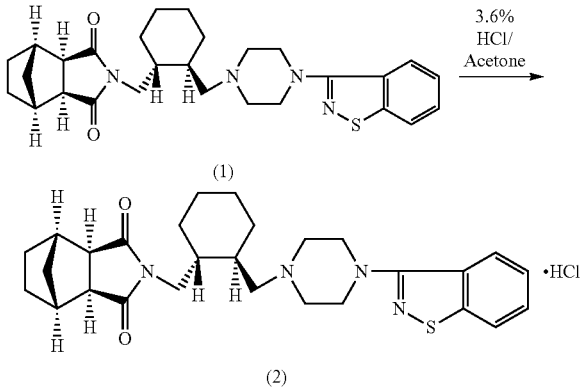

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide (8.25 g) was dissolved in acetone (102 g) with heating under reflux to give an acetone solution thereof. To this solution was added dropwise a 3.6% aqueous hydrochloric acid solution (18.5 g, 1.1 equivalent) over a period of about 15 minutes while the solution was kept at about 55° C. After the addition was completed, the reaction mixture was stirred at about 60° C. for one hour. The reaction mixture was cooled to 0° C., and stirred at the same temperature for one hour. The mixture was filtered, and the resulting solid was dried at room temperature under reduced pressure to give (1R,2S,3R,4S)-N-[(1R,2R)-2-[4-(1,2-benzisothiazol-3-yl)-1-piperazinylmethyl]-1-cyclohexylmethyl]-2,3-bicyclo-[2.2.1]heptanedicarboxyimide hydrochloride (7.5 g, yield: 85%).

EXAMPLE 2

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide (8.25 g) was dissolved in acetone (102 g) with heating under reflux to give an acetone solution thereof. To this acetone solution was added dropwise a 3.6% aqueous hydrochloric acid solution (18.5 g, 1.1 equivalent) at about 55° C. over a period of about 15 minutes. Then, the mixture was stirred at about 60° C. for one hour. The reaction mixture was cooled to 0° C., and stirred at the same temperature for one hour. The mixture was filtered, and the resulting solid was dried at room temperature under reduced pressure to give (1R,2S,3R,4S)-N-[(1R,2R)-2-[4-(1,2-benzisothiazol-3-yl)-1-piperazinylmethyl]-1-cyclohexylmethyl]-2,3-bicyclo[2.2.1]heptanedicarboxyimide hydrochloride (7.5 g, yield: 85%).

EXAMPLE 3

In the procedure in Example 2, a 3.6% aqueous hydrochloric acid solution (1.1 equivalent) was added dropwise over a period of one hour. (1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 2 except for the time for addition.

EXAMPLE 4

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide (3.5 g) was dissolved in acetone (43 g) with heating under reflux to give an acetone solution. To this acetone solution was added dropwise a 1.8% aqueous hydrochloric acid solution (1.1 equivalent) at about 55° C. over a period of about 5 minutes. Then, the mixture was stirred at about 60° C. for one hour. The reaction mixture was cooled to 0° C., and stirred at the same temperature for one hour. The mixture was filtered, and the resulting solid was dried at room temperature under reduced pressure to give (1R,2S,3R,4S)-N-[(1R,2R)-2-[4-(1,2-benzisothiazol-3-yl)-1-piperazinylmethyl]-1-cyclohexylmethyl]-2,3-bicyclo[2.2.1]heptanedicarboxyimide hydrochloride.

EXAMPLE 5

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 4 except that a 3.0% aqueous hydrochloric acid solution (1.1 equivalent) was used instead of the 1.8% aqueous hydrochloric acid solution (1.1 equivalent) in Example 4.

EXAMPLE 6

(1R,2S,3R,4S)-N-[(1R,2R)-2-[4-(1,2-Benzisothiazol-3-yl)-1)-1-piperazinylmethyl]-1-cyclohexylmethyl]-2,3-bicyclo[2.2.1]heptanedicarboxyimide hydrochloride was obtained in the same manner as in Example 4 except that a 3.6% aqueous hydrochloric acid solution (1.1 equivalent) was used instead of the 1.8% aqueous hydrochloric acid solution (1.1 equivalent) in Example 4.

EXAMPLE 7

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 4 except that a 4.2% aqueous hydrochloric acid solution (1.1 equivalent) was used instead of the 1.8% aqueous hydrochloric acid solution (1.1 equivalent) in Example 4.

EXAMPLE 8

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 4 except that a 5.0% aqueous hydrochloric acid solution (1.1 equivalent) was used instead of the 1.8% aqueous hydrochloric acid solution (1.1 equivalent) in Example 4.

EXAMPLE 9

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 1 except that a 5.0% aqueous hydrochloric acid solution (1.1 equivalent) was used instead of the 3.6% aqueous hydrochloric acid solution (1.1 equivalent) in Example 1.

EXAMPLE 10

A 5.0% aqueous hydrochloric acid solution (1.1 equivalent) was added dropwise over a period of one hour instead of the 3.6% aqueous hydrochloric acid solution (1.1 equivalent) in Example 2. (1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 2 except for the time for addition and the concentration of the aqueous hydrochloric acid solution.

EXAMPLE 11

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 4 except that a 7.2% aqueous hydrochloric acid solution (1.1 equivalent) was used instead of the 1.8% aqueous hydrochloric acid solution (1.1 equivalent) in Example 4.

EXAMPLE 12

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 4 except that a 14.4% aqueous hydrochloric acid solution (1.1 equivalent) was used instead of the 1.8% aqueous hydrochloric acid solution (1.1 equivalent) in Example 4.

EXAMPLE 13

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 4 except that a 36% aqueous hydrochloric acid solution (1.1 equivalent) was used instead of the 1.8% aqueous hydrochloric acid solution (1.1 equivalent) in Example 4.

EXAMPLE 14

In the procedure of Example 1, a solution of (1R,2S,3R,4S)-N-[(1R,2R)-2-[4-(1,2-benzisothiazol-3-yl)-1-piperazinylmethyl]-1-cyclohexylmethyl]-2,3-bicyclo[2.2.1]heptanedicarboxyimide (8.25 g) in acetone was added dropwise into a 3.6% aqueous hydrochloric acid solution (18.5 g, 1.1 equivalent) over a period of one hour. (1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride was obtained in the same manner as in Example 1 except for the method of addition.

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide hydrochloride obtained in Examples 1-14 was analyzed, and the results thereof are shown in Table 1.

TABLE 1

| | Ex. No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Conc. of aq. HCl solution (% by weight) | 3.6% | 3.6% | 3.6% | 1.8% | 3.0% | 3.6% | 4.2% | 5.0% | 5.0% | 5.0% | 7.2% | 14.4% | 36% | 3.6% |
| Yield | 85% | 85% | 85% | 65% | 84% | 85% | 89% | 90% | 90% | 90% | 96% | 97% | 97% | 85% |
| Acetone in the crystals (% by weight) | 0.1% | 0.1% | 0.1% | 0.1% | 0.1% | 0.1% | 0.1% | 0.1% | 0.1% | 0.1% | 0.5% | 0.5% | 1.0% | 0.1% |
| Amount of impurities in the crystals | 0.1% | 0.1% | 0.1% | 0.1% | 0.1% | 0.1% | 0.1% | 0.1% | 0.1% | 0.1% | 0.1% | 0.1% | 0.2% | 0.1% |

The amounts of acetone in the crystals were determined by gas chromatography using a capillary column and FID detector, and the amounts of impurities were determined by liquid chromatography using a reversed phase ODS column and a UV detector.

EXAMPLE 15

(1R,2 S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide (1.5 g) was dissolved in tetrahydrofuran (5.5 g) with heating under reflux to give a tetrahydrofuran solution. To this solution was added a 3.6% hydrochloric acid (6.18 g) under reflux, and the reaction mixture was cooled to 20° C., filtered, and the resulting solid was dried under reduced pressure to give (1R,2S,3R,4S)-N-[(1R,2R)-2-[4-(1,2-benzisothiazol-3-yl)-1-piperazinylmethyl]-1-cyclohexylmethyl]-2,3-bicyclo-[2.2.1]heptanedicarboxyimide hydrochloride (1.34 g, yield: 83%).

EXAMPLE 16

(1R,2S,3R,4S)-N-[(1R,2R)-2-[4-(1,2-Benzisothiazol-3-yl)-1-piperazinylmethyl]-1-cyclohexylmethyl]-2,3-bicyclo[2.2.1]heptanedicarboxyimide (2.0 g) was dissolved in methyl ethyl ketone (22 g) with heating at about 60° C. to give a methyl ethyl ketone solution. To this solution was added a 3.6% hydrochloric acid (4.52 g) at about 60° C., and the reaction mixture was cooled to 0° C. The reaction mixture was filtered, and the resulting solid was dried under reduced pressure at room temperature to give (1R,2S,3R,4S)-N-[(1R,2R)-2-[4-(1,2-benzisothiazol-3-yl)-1-piperazinylmethyl]-1-cyclohexylmethyl]-2,3-bicyclo[2.2.1]heptanedicarboxyimide hydrochloride (0.84 g, yield: 39%).

EXAMPLE 17

(1R,2S,3R,4S)-N-[(11R,2R)-2-[4-(1,2-Benzisothiazol-3-yl)-1-piperazinylmethyl]-1-cyclohexylmethyl]-2,3-bicyclo[2.2.1]heptanedicarboxyimide (2.0 g) was dissolved in 2-propanol (200 g) with heating at about 80° C. to give a 2-propanol solution. To this solution was added a 14.4% hydrochloric acid (1.54 g) at about 80° C., and the reaction mixture was cooled to 0° C. The reaction mixture was filtered, and the resulting solid was dried under reduced pressure at room temperature to give (1R,2S,3R,4S)-N-[(1R,2R)-2-[4-(1,2-benzisothiazol-3-yl)-1-piperazinylmethyl]-1-cyclohexylmethyl]-2,3-bicyclo[2.2.1]heptanedicarboxyimide hydrochloride (2.05 g, yield: 95%).

INDUSTRIAL APPLICABILITY

According to the present invention, it becomes possible to provide an industrially advantageous process for producing the imide compound hydrochloride of the above formula (2).

The invention claimed is:

1. A process for producing an imide compound hydrochloride of the formula (2):

(2)

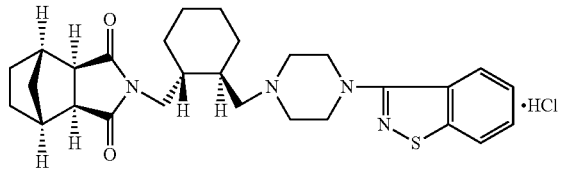

or an enantiomer thereof, which comprises treating a compound of the formula (1):

(1)

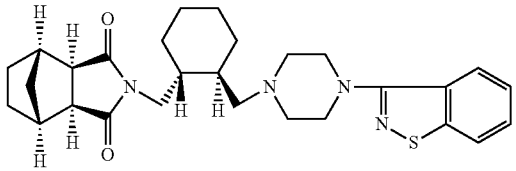

or an enantiomer thereof with 1.8 to 5.0% aqueous hydrochloric acid solution in acetone, crystallizing the resultant hydrochloride of the formula (2), and isolating the crystallized hydrochloride of the formula (2).

2. The process for producing the imide compound hydrochloride according to claim 1, wherein the aqueous hydrochloric acid solution is a 3.0-5.0% aqueous hydrochloric acid solution.

*3. The imide compound hydrochloride of the formula (2)*

*(2)*

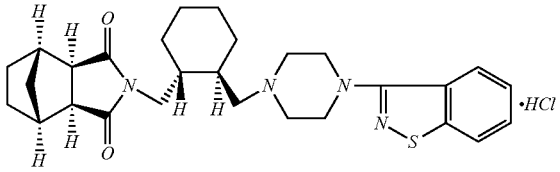

*which is obtained by the process according to claim 1 or 2.*

*4. The imide compound hydrochloride as set forth in claim 3, which has a residual acetone content of about 0.1% by weight or less.*

*5. The imide compound hydrochloride as set forth in claim 3, which has impurities of about 0.1% by weight or less.*

*6. The imide compound hydrochloride as set forth in claim 3, which has a residual acetone content of about 0.1% by weight or less, and which has impurities of about 0.1% by weight or less.*

*7. A process for producing an imide compound hydrochloride of the formula (2):*

*(2)*

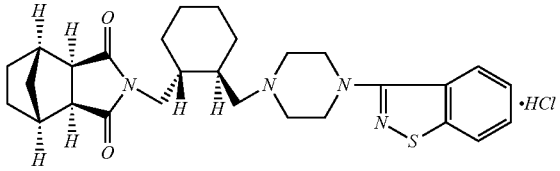

*which comprises treating a compound of the formula (1):*

*(1)*

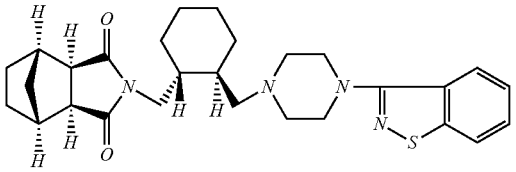

*with 1.8 to 5.0% aqueous hydrochloric acid solution in acetone, crystallizing the resultant hydrochloride of the formula (2), and isolating the crystallized hydrochloride of the formula (2).*

*8. The process for producing the imide compound hydrochloride according to claim 7, wherein the aqueous hydrochloric acid solution is a 3.0-5.0% aqueous hydrochloric acid solution.*

*9. The imide compound hydrochloride of the formula (2)*

*(2)*

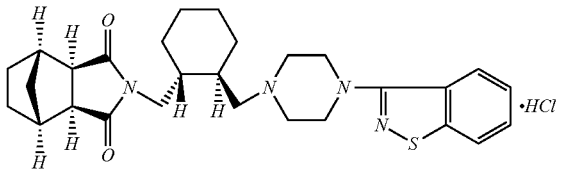

*which is obtained by the process according to claim 7 or 8.*

*10. The imide compound hydrochloride as set forth in claim 9, which has a residual acetone content of about 0.1% by weight or less.*

*11. The imide compound hydrochloride as set forth in claim 9, which has impurities of about 0.1% by weight or less.*

*12. The imide compound hydrochloride as set forth in claim 9, which has a residual acetone content of about 0.1% by weight or less, and which has impurities of about 0.1% by weight or less.*

* * * * *